(12) United States Patent
Chang et al.

(10) Patent No.: US 9,398,874 B2
(45) Date of Patent: Jul. 26, 2016

(54) MOOD ANALYSIS METHOD, SYSTEM, AND APPARATUS

(71) Applicants: Chiun Mai Communication Systems, Inc., New Taipei (TW); YongLin Biotech Corp., New Taipei (TW)

(72) Inventors: Ming-Shiung Chang, New Taipei (TW); Hsun-Ko Chan, New Taipei (TW); Daniel M Weng, Santa Clara, CA (US); Shu-Chen Chuang, New Taipei (TW); Tuan-Chun Chen, New Taipei (TW); Pei-Chi Ho, New Taipei (TW); Hsiang-I Kao, New Taipei (TW); Shing-Huei Lin, New Taipei (TW)

(73) Assignees: Chiun Mai Communication Systems, Inc., New Taipei (TW); YongLin Biotech Corp., New Taipei (TW)

( * ) Notice: Subject to any disclaimer, the term of this patent is extended or adjusted under 35 U.S.C. 154(b) by 0 days.

(21) Appl. No.: 14/253,822

(22) Filed: Apr. 15, 2014

(65) Prior Publication Data

US 2015/0025403 A1    Jan. 22, 2015

(30) Foreign Application Priority Data

Apr. 15, 2013 (TW) ................................ 102113369

(51) Int. Cl.
*A61B 5/04* (2006.01)
*A61B 5/16* (2006.01)
*A61B 5/0456* (2006.01)
*A61B 5/00* (2006.01)

(52) U.S. Cl.
CPC ............... *A61B 5/165* (2013.01); *A61B 5/0456* (2013.01); *A61B 5/7257* (2013.01)

(58) Field of Classification Search
CPC ......... A61B 5/0456; A61B 5/743; A61B 5/40
See application file for complete search history.

(56) References Cited

U.S. PATENT DOCUMENTS

| 6,292,688 | B1 * | 9/2001 | Patton .................... A61B 5/16 600/300 |
| 8,298,131 | B2 | 10/2012 | Chung et al. |
| 2004/0111036 | A1 * | 6/2004 | Nissila ................ A61B 5/0006 600/509 |
| 2005/0272984 | A1 * | 12/2005 | Huiku ........................... 600/301 |
| 2009/0292180 | A1 * | 11/2009 | Mirow ................. G06F 19/363 600/301 |
| 2010/0174205 | A1 * | 7/2010 | Wegerif ...................... 600/515 |
| 2010/0198092 | A1 * | 8/2010 | Jimenez-Acquarone ....... A61B 5/02405 600/515 |
| 2013/0144181 | A1 * | 6/2013 | Fogt et al. .................... 600/521 |

FOREIGN PATENT DOCUMENTS

| TW | 524670 | 3/2003 |
| TW | M386552 | 8/2010 |

* cited by examiner

*Primary Examiner* — Christopher D Koharski
*Assistant Examiner* — Natasha Patel
(74) *Attorney, Agent, or Firm* — ScienBiziP, P.C.

(57) ABSTRACT

In a mood analysis method using an electrocardiogram of a user, RR intervals in the electrocardiogram are computed, and low-frequency (LF) values and high-frequency (HF) values are also computed according to the RR intervals. Standard values of sympathetic nervous system (SNS) activity and parasympathetic nervous system (PSNS) activity are acquired corresponding to age and sex data of the user, to establish a mood display coordinate system. Coordinates of the LF values and the HF values in the mood display coordinate system are computed to determine a mood of the user.

15 Claims, 4 Drawing Sheets

MOOD ANALYSIS METHOD, SYSTEM, AND APPARATUS

FIELD

Embodiments of the present disclosure relate to an electrocardiogram (ECG) analysis technique, and more specifically relates to an apparatus, a method, and a system to analyze an ECG of a user to determine a mood of the user.

BACKGROUND

An electrocardiogram (ECG) is used to measure the heart's electrical conduction system. The ECG measures electrical impulses generated by the polarization and depolarization of cardiac tissue, and translates the electrical impulses into a wave, which is used to measure the rate and regularity of heartbeats. The wave comprises a P wave, a QRS complex, a T wave, and a U wave. The QRS complex includes a plurality of R waves.

A RR interval, namely the interval between two adjacent R waves, can be used to measure a heart rate. The heart rate can vary due to physical exercise, mood, and so on.

Usually, the ECG can only be read by experts, for example medical staffs.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean "at least one." The references "a plurality of" and "a number of" mean "at least two.

In general, the word "module," as used hereinafter, refers to logic embodied in hardware or firmware, or to a collection of software instructions, written in a programming language, such as, for example, Java, C, or assembly. One or more software instructions in the modules may be embedded in firmware. It will be appreciated that modules may comprise connected logic units, such as gates and flip-flops, and may comprise programmable units, such as programmable gate arrays or processors. The modules described herein may be implemented as either software and/or hardware modules and may be stored in any type of non-transitory computer-readable storage medium or other computer storage device.

Figure 1:
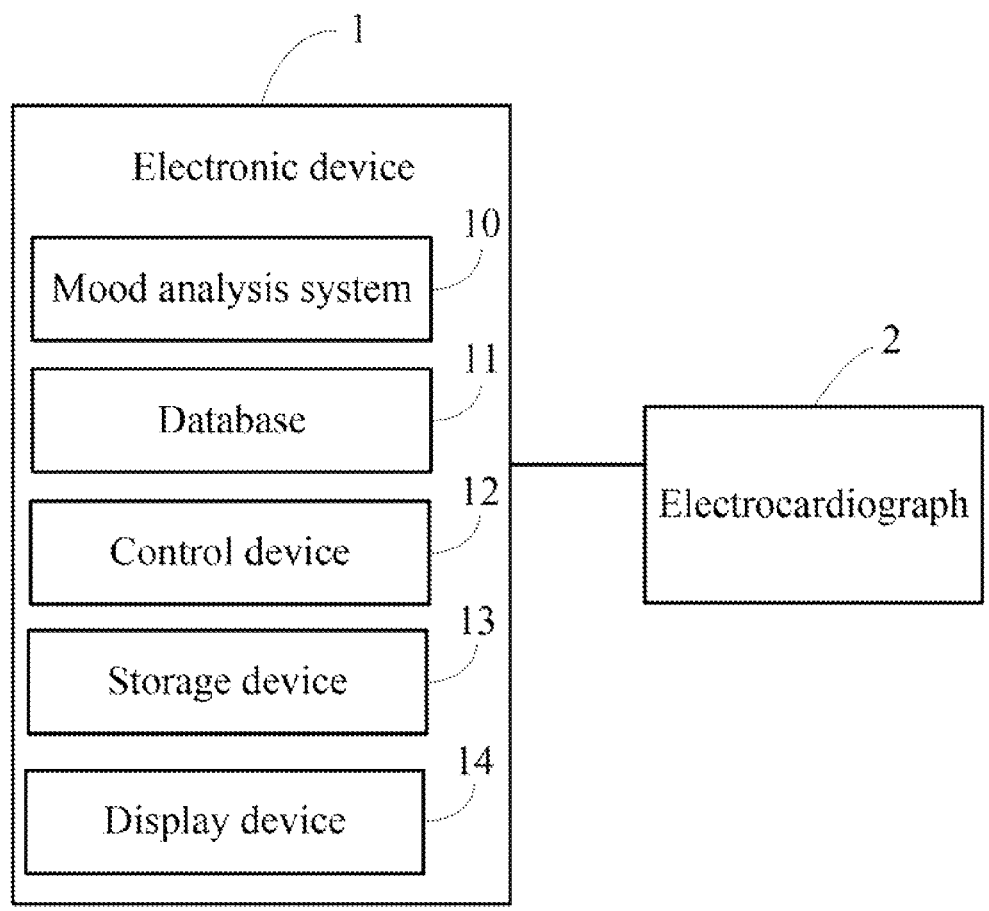
FIG. 1 is a block diagram of one example embodiment of a hardware environment for executing a mood analysis system.

FIG. 1 is a block diagram of one embodiment of a hardware environment for executing a mood analysis system 10. The mood analysis system 10 is installed and ran on an electronic device 1, for example a computer, a smart phone, server, or a smart TV. The electronic device 1 can include a database 11, a control device 12, a storage device 13, and a display device 14. In one embodiment, the electronic device 1 is electrically connected to an electrocardiograph 2 for receiving an electrocardiogram (ECG) of one or more users.

The mood analysis system 10 can include a plurality of function modules (shown in FIG. 2) that analyze and display moods of users in accordance to users' ECGs.

The database 11 can be installed in the electronic device 1 or be externally connected with the electronic device 1. The database 11 stores standard values of the sympathetic nervous system (SNS) activity and the parasympathetic nervous system (PSNS) activity of users corresponding to a user's age and sex.

The control device 12 can be a processor, an application-specific integrated circuit (ASIC), or a field programmable gate array (FPGA), for example. The control device 12 can execute computerized codes of the function modules of the mood analysis system 10 to realize the functions of the electronic device 1.

The storage device 13 can include some type(s) of non-transitory computer-readable storage medium, for example a hard disk drive, a compact disc, a digital video disc, or a tape drive. The storage device 13 stores the computerized codes of the function modules of the mood analysis system 10.

Figure 2:
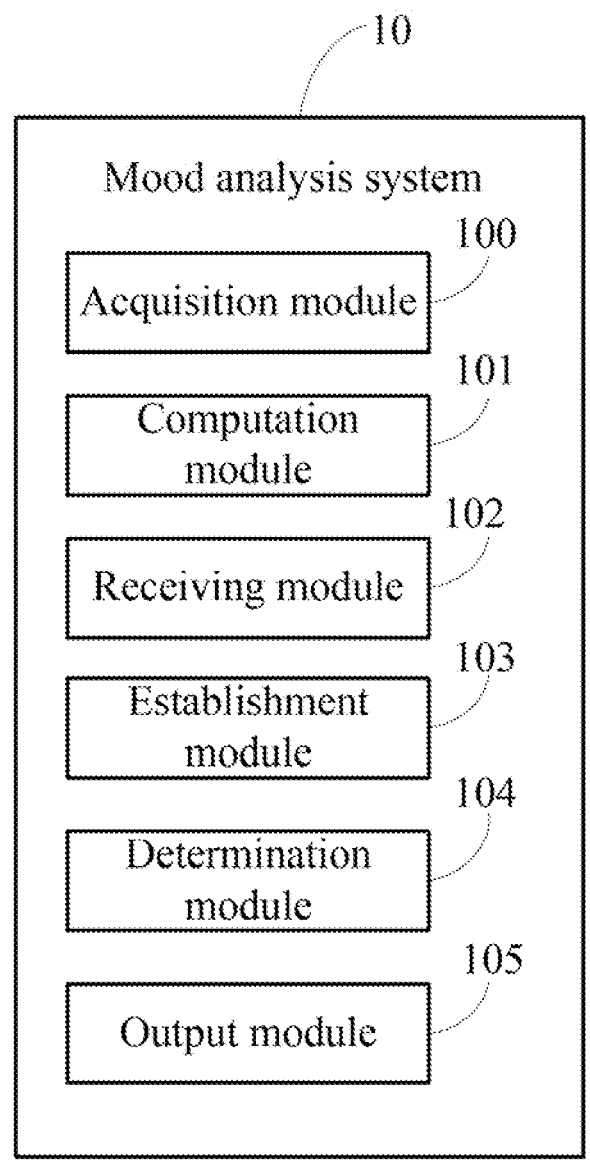
FIG. 2 is a block diagram of one example embodiment of function modules of the mood analysis system in FIG. 1.

FIG. 2 is a block diagram of one embodiment of function modules of the mood analysis system 10. The function modules can includes an acquisition module 100, a computation module 101, a receiving module 102, an establishment module 103, a determination module 104, and an output module 105. The function modules 100-105 can include computerized codes in the form of one or more programs, which provide at least the functions needed to execute the steps illustrated in FIG. 3.

Figure 3:
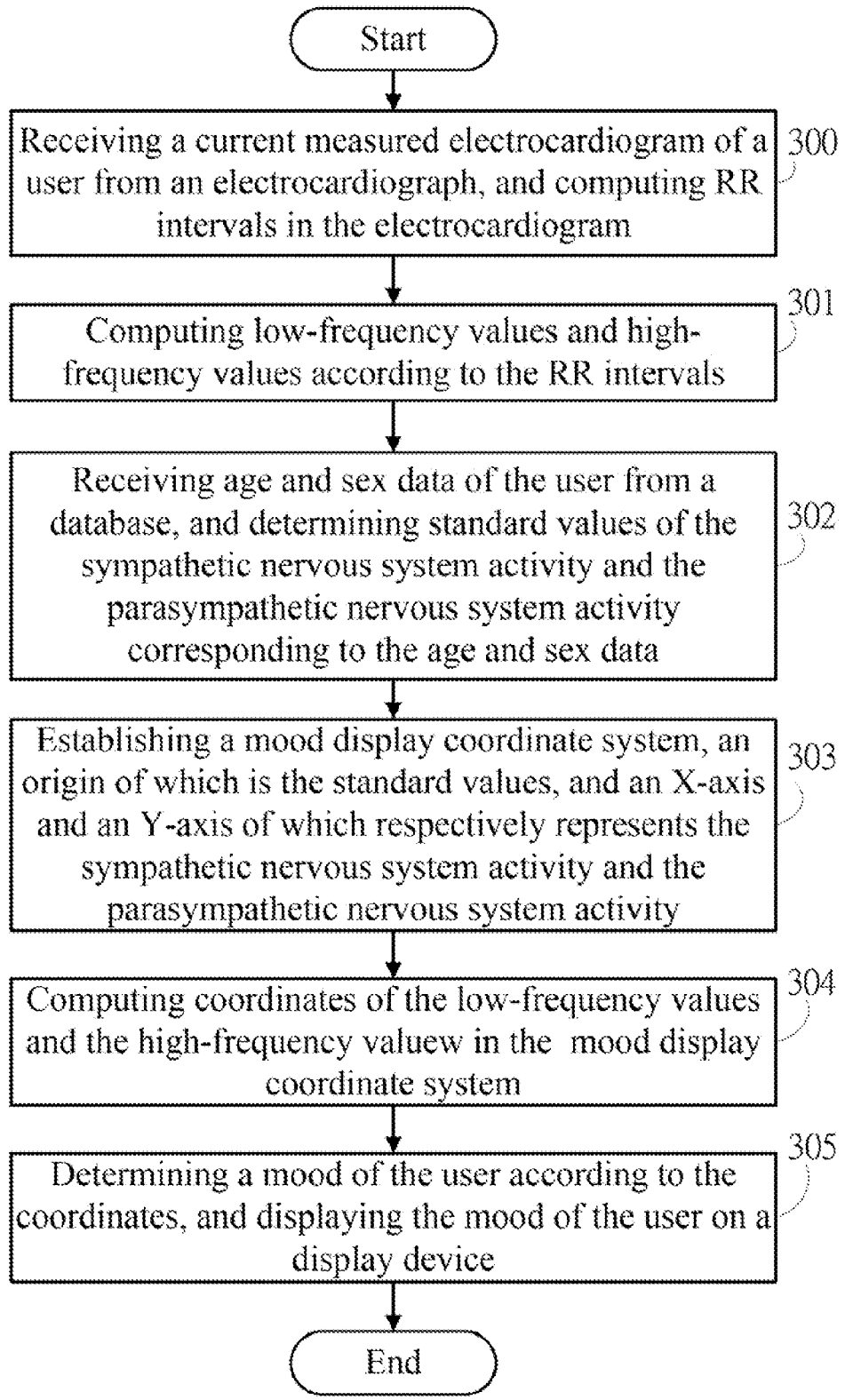
FIG. 3 is a flowchart of one example embodiment of a mood analysis method.

FIG. 3 is a flowchart of one example embodiment of a mood analysis method. In the embodiment, the method is performed by execution of computer-readable software program codes or instructions by at least one processor (i.e., the control device 12) of the electronic device 1. Depending on the embodiment, additional steps in FIG. 3 can be added, removed, and the ordering of the steps can be changed.

In 300, the acquisition module 100 receives a current measured electrocardiogram of a user from the electrocardiograph 2, and determines RR intervals in the electrocardiogram. In the embodiment, the RR interval is defined as an interval between two adjacent R waves in the electrocardiogram.

In 301, the computation module 101 computes low-frequency (LF) values and high-frequency (HF) values according to the RR intervals using Fourier transformation. The LF values represent current values of SNS activity, and the HF values represent current values of PSNS activity of the user.

In 302, the receiving module 102 acquires age and sex data of the user from the database 11, and determines standard values of the SNS activity and the PSNS activity corresponding to the age and sex data of the user. The age and sex data can be input by the user through a user interface (UI), or can be received from the database 11.

Figure 4:
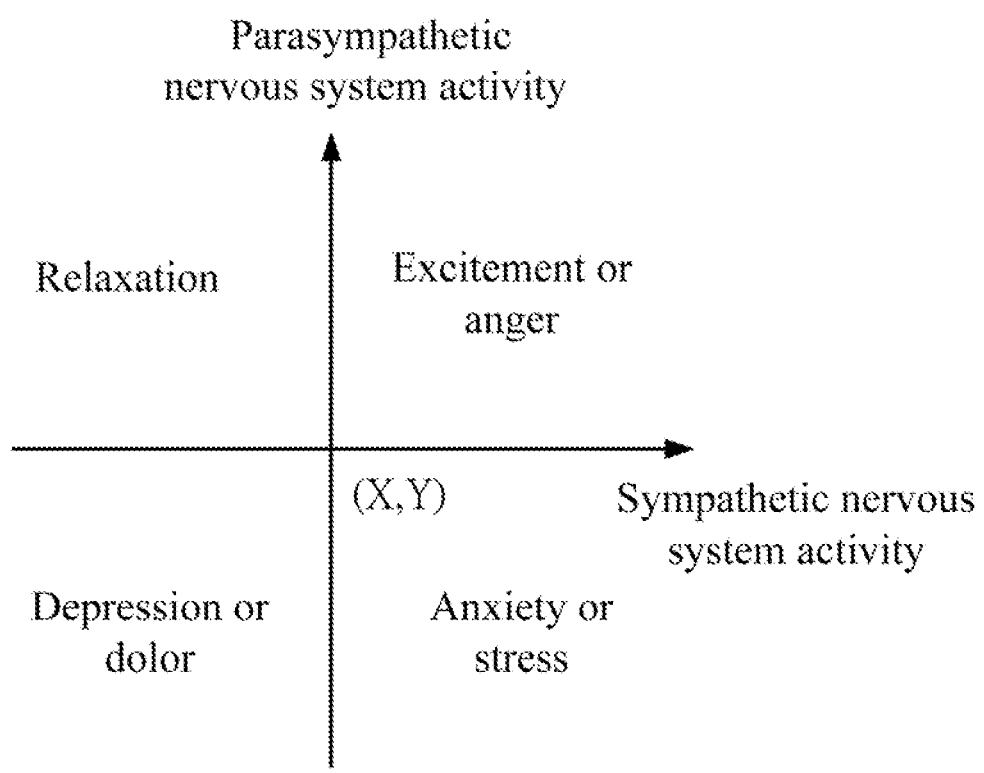
FIG. 4 illustrates an example mood display coordinate system.

In 303, the establishment module 103 establishes a mood display coordinate system, wherein an origin of the mood display coordinate system is the standard values of the SNS activity and the PSNS activity corresponding to the age and sex data of the user, and an X-axis and Y-axis of the mood display coordinate system respectively represent the SNS activity and the PSNS activity. FIG. 4 illustrates an example mood display coordinate system. Coordinates in the first quadrant of the mood display coordinate system can represent excitement or anger. Coordinates in the second quadrant can represent relaxation. Coordinates in the third quadrant can represent depression or dolor. Coordinates in the fourth quadrant can represent anxiety and stress.

In 304, the determination module 104 computes coordinates of the LF values and the HF values in the mood display coordinate system. The coordinates (X, Y) of the LF values and the HF values are represented by the following equations:

$X$=LF values−the standard values of the SNS activity;

$Y$=HF values−the standard values of the PSNS activity.

In 305, the output module 105 determines a current mood of the user according to the computed coordinates, and displays the mood of the user on the display device 14. When the coordinates of the LF values and the HF values are in the first quadrant of the mood display coordinate system, the output module 105 determines that the current mood of the user is excitement or anger. When the coordinates of the LF values and the HF values are in the second quadrant of the mood display coordinate system, the output module 105 determines that the current mood of the user is relaxation. When the coordinates of the LF values and the HF values are in the third quadrant of the mood display coordinate system, the output module 105 determines that the current mood of the user is depression or dolor. When the coordinates of the LF values and the HF values are in the fourth quadrant of the mood display coordinate system, the output module 105 determines that the current mood of the user is anxiety or stress.

It should be emphasized that the above-described embodiments of the present disclosure, including any particular embodiments, are merely possible examples of implementations, set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

What is claimed is:

1. A mood analysis method being executed by at least one processor of an electronic device, the method comprising:
    measuring an electrocardiogram of a user using an electrocardiograph, and detecting RR intervals in the electrocardiogram;
    computing low-frequency (LF) values and high-frequency (HF) values according to the RR intervals;
    receiving age and sex data of the user from a database, and generating standard values of sympathetic nervous system (SNS) activity and parasympathetic nervous system (PSNS) activity corresponding to the age and sex data of the user;
    establishing a mood display coordinate system using the standard values of the SNS activity and the PSNS activity;
    detecting coordinates of the LF values and the HF values in the mood display coordinate system; and
    analyzing a current mood of the user according to the computed coordinates, and outputting the mood of the user to a display device of the electronic device for displaying the mood for the user.

2. The method according to claim 1, further comprising:
    storing standard values of the SNS activity and the PSNS activity of users corresponding to different age and sex data into the database which is installed in the electronic device or externally connected with the electronic device.

3. The method according to claim 1, wherein an origin of the mood display coordinate system is the standard values of the SNS activity and the PSNS activity corresponding to the age and sex data of the user, and an X-axis and an Y-axis of the mood display coordinate system respectively represent the SNS activity and the PSNS activity.

4. The method according to claim 1, wherein the coordinates (X, Y) of the LF values and the HF values are computed by:

$X$=LF values−the standard values of the SNS activity; and $Y$=HF values−the standard values of the PSNS activity.

5. The method according to claim 1, wherein the current mood of the user is determined as excitement or anger when the coordinates of the LF values and the HF values are in a first quadrant of the mood display coordinate system, the current mood of the user is determined as relaxation when the coordinates of the LF values and the HF values are in the second quadrant of the mood display coordinate system, the current mood of the user is determined as depression or dolor when the coordinates of the LF values and the HF values are in a third quadrant of the mood display coordinate system, and the current mood of the user is determined as anxiety or stress when the coordinates of the LF values and the HF values are in a fourth quadrant of the mood display coordinate system.

6. An apparatus, comprising:
    an electrocardiograph configured to measure an electrocardiogram of a user;
    a display device;
    a control device; and
    a storage device storing one or more programs which when executed by the control device, causes the control device to:
        receive a current measured electrocardiogram of the user from the electrocardiograph, and detect RR intervals in the electrocardiogram;
    compute low-frequency (LF) values and high-frequency (HF) values according to the RR intervals;
    receive age and sex data of the user from a database, and generate standard values of sympathetic nervous system (SNS) activity and parasympathetic nervous system (PSNS) activity corresponding to the age and sex data of the user;
    establish a mood display coordinate system using the standard values of the SNS activity and the PSNS activity;
    detect coordinates of the LF values and the HF values in the mood display coordinate system; and
    analyze a current mood of the user according to the computed coordinates, and output the mood of the user to the display device for displaying the mood for the user.

7. The apparatus according to claim 6, wherein
    the database is installed in the electronic device or externally connected with the electronic device, and stores standard values of the SNS activity and the PSNS activity of users corresponding to different age and sex data.

8. The apparatus according to claim 6, wherein an origin of the mood display coordinate system is the standard values of the SNS activity and the PSNS activity corresponding to the age and sex data of the user, and an X-axis and an Y-axis of the mood display coordinate system respectively represent the SNS activity and the PSNS activity.

9. The apparatus according to claim 6, wherein the coordinates (X, Y) of the LF values and the HF values are computed by:

$X$=LF values–the standard values of the SNS activity; and $Y$=HF values–the standard values of the PSNS activity.

10. The apparatus according to claim 6, wherein when the coordinates of the LF values and the HF values are in the first quadrant of the mood display coordinate system, the current mood of the user is determined as excitement or anger, when the coordinates of the LF values and the HF values are in the second quadrant of the mood display coordinate system, the current mood of the user is determined as relaxation, when the coordinates of the LF values and the HF values are in the third quadrant of the mood display coordinate system, the current mood of the user is determined as depression or dolor, and when the coordinates of the LF values and the HF values are in the fourth quadrant of the mood display coordinate system, the current mood of the user is determined as anxiety or stress.

11. An electronic device for being electronically connected to an electrocardiograph and for receiving an electrocardiogram of a user from the electrocardiograph, comprising:

a database for storing standard values of sympathetic nervous system (SNS) activity and parasympathetic nervous system (PSNS) activity of the user; and a mood analysis system, including:

an acquisition module for receiving the electrocardiogram from the electrocardiograph and determining RR intervals in the electrocardiogram;

a computation module for computing low-frequency (LF) values and high-frequency (HF) values according to the RR intervals;

an establishment module for establishing a mood display coordinate system using the standard values of the SNS activity and the PSNS activity;

a determination module for computing coordinates of the LF values and the HF values in the mood display coordinate system; and an output module for determining a mood of the user according to the computed coordinates, wherein at least one of the acquisition module, the computation module, the establishment module, the determination module and the output module includes computerized codes in the form of one or more programs;

a control device for executing the computerized codes; and a display device for displaying the determined mood.

12. The electronic device according to claim 11, wherein the database further comprises age and sex data of the user.

13. The electronic device according to claim 12, wherein the mood analysis system further includes a receiving module for acquiring the age and sex data of the user from the database and determining the standard values of the SNS activity and the PSNS activity corresponding to the age and sex data of the user.

14. The electronic device according to claim 11, wherein the coordinates of the LF values and the HF values are computed by:

$X$=LF values–the standard values of the SNS activity; and $Y$=HF values–the standard values of the PSNS activity.

15. The electronic device according to claim 11, wherein when the coordinates of the LF values and the HF values are in the first quadrant of the mood display coordinate system, the current mood of the user is determined as excitement or anger, when the coordinates of the LF values and the HF values are in the second quadrant of the mood display coordinate system, the current mood of the user is determined as relaxation, when the coordinates of the LF values and the HF values are in the third quadrant of the mood display coordinate system, the current mood of the user is determined as depression or dolor, and when the coordinates of the LF values and the HF values are in the fourth quadrant of the mood display coordinate system, the current mood of the user is determined as anxiety or stress.

* * * * *